(12) United States Patent
Hurwitz et al.

(10) Patent No.: US 12,394,525 B2
(45) Date of Patent: Aug. 19, 2025

(54) ACTIVE HIDDEN STRESSOR IDENTIFICATION AND NOTIFICATION

(71) Applicant: Google LLC, Mountain View, CA (US)

(72) Inventors: Jonathan D. Hurwitz, San Jose, CA (US); Diane Wang, San Francisco, CA (US)

(73) Assignee: Google LLC, Mountain View, CA (US)

( * ) Notice: Subject to any disclaimer, the term of this patent is extended or adjusted under 35 U.S.C. 154(b) by 950 days.

(21) Appl. No.: 17/331,077

(22) Filed: May 26, 2021

(65) Prior Publication Data
US 2022/0384034 A1     Dec. 1, 2022

(51) Int. Cl.
G06N 20/00     (2019.01)
G06N 20/10     (2019.01)
G16H 40/63     (2018.01)
G16H 50/20     (2018.01)

(52) U.S. Cl.
CPC ............. *G16H 50/20* (2018.01); *G06N 20/00* (2019.01); *G06N 20/10* (2019.01); *G16H 40/63* (2018.01)

(58) Field of Classification Search
CPC ........ G16H 50/20; G16H 40/63; G06N 20/00; G06N 20/10
See application file for complete search history.

(56) References Cited

U.S. PATENT DOCUMENTS

| 2014/0052682 | A1 | 2/2014 | Phan et al. |
| 2014/0366049 | A1 | 12/2014 | Lehtiniemi et al. |
| 2016/0302711 | A1* | 10/2016 | Frank ............... A61B 5/746 |
| 2020/0201434 | A1* | 6/2020 | Aliamiri ............ G06N 3/088 |
| 2022/0101593 | A1* | 3/2022 | Rockel ............. A63F 13/426 |

FOREIGN PATENT DOCUMENTS

JP     2010220151 A     9/2010

OTHER PUBLICATIONS

International Preliminary Report on Patentability for International Application No. PCT/US2022/030909 dated Dec. 7, 2023. 9 pages.
Zhai et al. Stress Detection in Computer Users Based on Digital Signal Processing of Noninvasive Physiological Variables. Aug. 30-Sep. 3, 2006. Conference Proceedings. Annual International Conference of the IEEE Engineering in Medicine and Biology Society (IEEE Cat. No. 06CH37748); New York, NY, USA, IEEE, Piscataway, NJ, USA, pp. 1355-1358.
Alharthi et al. CASP: context-aware stress prediction system. Oct. 7, 2017. Multimedia Tools and Applications, Kluwer Academic Publishers, Boston, US, vol. 78, No. 7, pp. 9011-9031.

(Continued)

*Primary Examiner* — Andrew T McIntosh
(74) *Attorney, Agent, or Firm* — Lerner David LLP

(57) ABSTRACT

A local and private model can be used to analyze textual, visual, and auditory content on a user's local device to provide notifications about events which are stressful beyond a predetermined threshold. The model can be trained by a combination of health sensor data and an analysis of the content. Multiple models or techniques can be used to analyze the content and vectorize the content. A vector based approach can be used to classify future content as stressful when meeting the predetermined threshold.

20 Claims, 8 Drawing Sheets

(56) References Cited

OTHER PUBLICATIONS

Birjali et al. A comprehensive survey on sentiment analysis: Approaches, challenges and trends. May 14, 2021. Knowledge-Based Systems, Elsevier, Amsterdam, NL, vol. 226, 26 pages.
Bota et al. A Review, Current Challenges, and Future Possibilities on Emotion Recognition Using Machine Learning and Physiological Signals. Sep. 26, 2019. IEEE Access, vol. 7, pp. 140990-141020.
Bobade et al. Stress Detection with Machine Learning and Deep Learning using Multimodal Physiological Data. Jul. 15, 2020. 2020 Second International Conference on Inventive Research in Computing Applications (ICIRCA), IEEE, pp. 51-57.
International Search Report and Written Opinion for International Application No. PCT/US2022/030909 dated Sep. 12, 2022. 15 pages.
Lin et al., "Detecting Stress Based on Social Interactions in Social Networks," IEEE Transactions on Knowledge and Data Engineering, Sep. 2017, 29(9): 1820-1833, IEEE.
Luo, "Network text sentiment analysis method combining LDA text representation and GRU-CNN," Personal and Ubiquitous Computing, 2019, 23:405-412, Springer.
Song et al., "Taxonomic Classification for Web-based Videos," Google LLC. [Retrieved Jan. 21, 2021].Retrieved from the internet <https://static.googleusercontent.com/media/research.google.com/en//pubs/archive/36411.pdf>, 8 bages.
Office Action for Japanese Patent Application No. 2023-572853 dated Dec. 3, 2024. 4 pages.
Office Action for Japanese Patent Application No. 2023-572853 dated May 27, 2025, 5 pages.

\* cited by examiner

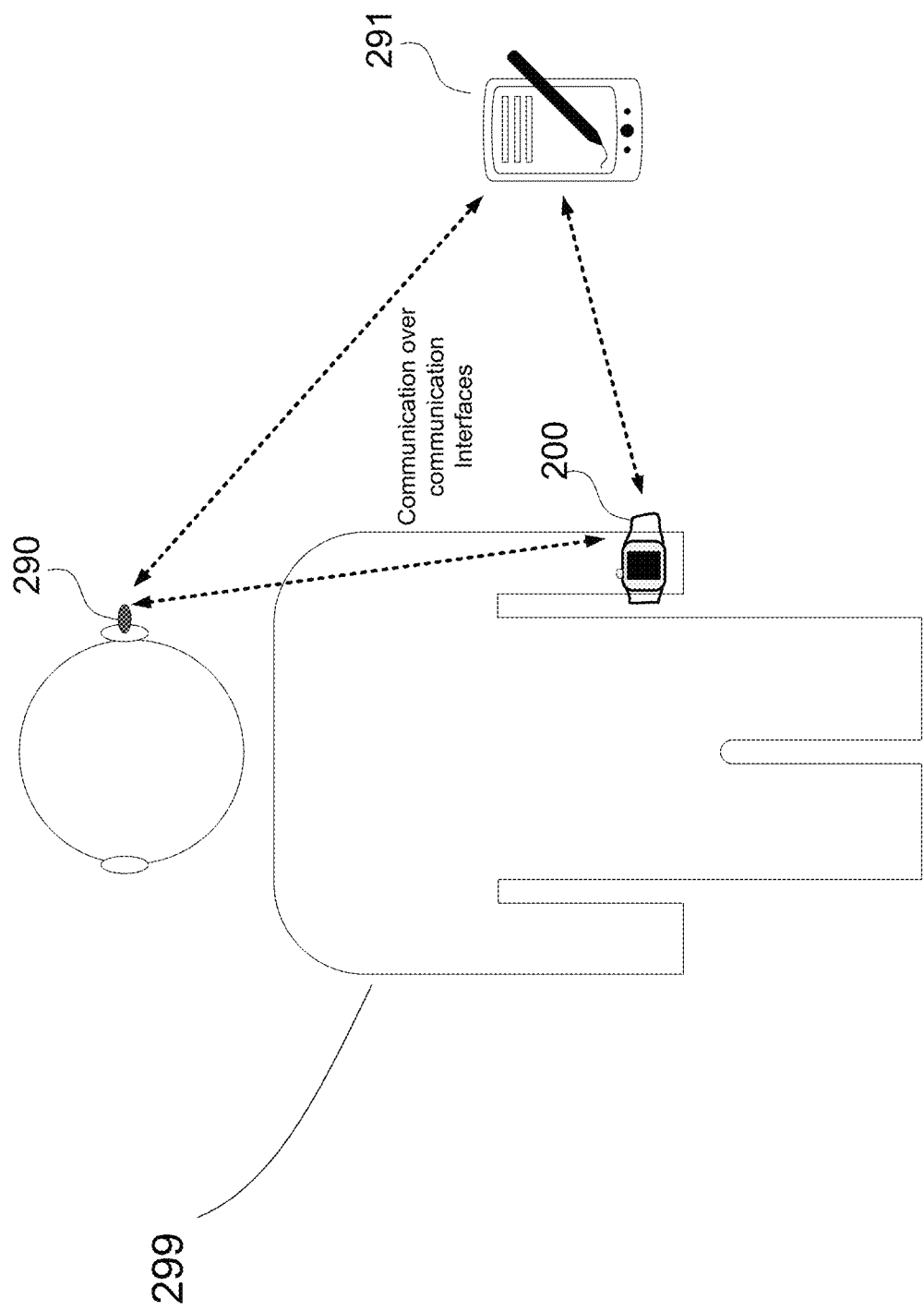

300

400

ACTIVE HIDDEN STRESSOR IDENTIFICATION AND NOTIFICATION

BACKGROUND

Mental health stressors are difficult to identify and track but understanding them is important to maintaining overall well-being. As computing becomes more ubiquitous, people may be able to obtain specific understanding and control over stressful content and situations that computing devices may expose them to. In more detail, specific types of content across news, messaging, and social media have been shown to cause stress and have a negative impact on user well-being.

Notifications related to "screen time" or "activity" are not tied to live or active health information or the underlying content. In this manner, the mental, subconscious, or psychological impact of stressors contained within media, applications, or content is not recognized and often can go undetected or unnoticed by a user.

SUMMARY

Aspects of the present disclosure include methods, systems, and apparatuses for active hidden stressor identification and notification.

An aspect of the disclosed technology may comprise a method for determining health stressors. The method may comprise receiving input information comprising one or more of text information displayed on a user device of a user and image data displayed on the user device; receiving health information at a given time marker from a wearable device associated with the user; associating at least one of the text information and image information with the given time marker based on a determination that the received health information is at least a threshold value; and correlating, using a model, other text information or other image information to the text information or the image information based on the received health information. The method may also comprise generating a stress indicator based on a determination that the other text information and other image information are correlated to the text information and the image information associated with the received health information.

In accordance with this aspect of the disclosed technology, the method may for example comprise classifying the text information to produce a first numerical value; determining a topic category associated with the text information to produce a second numerical value; classifying the image data to produce a third numerical value; and forming a first vector comprising the first, second, and third numerical values and the received health information. Further in accordance with this aspect of the technology, correlating may comprise searching a vector space having a plurality of vectors using the received health information of the first vector. Further in accordance with this aspect of the technology, classifying the text information may comprise classifying the text information using a sentiment classifier. Additionally, an output of the sentiment classifier may be mapped to numerical values including the first numerical value. Moreover, the sentiment classifier may comprise one of a Support Vector Machine (SVM), a Bayesian classifier or Long Short Term Memory (LSTM) derived model.

In accordance with the method image data, may, for example, comprise video or still image data. In some examples, the image data may be viewable through an application on the user device. In some examples, health information may comprise one or more of a heart rate, heart rate variability, temperature, stress from EDA activity, user motion, and sleep data.

In accordance with the method, the stress indicator may comprise a message that notifies the user of the stressor event.

Another aspect of the disclosed technology may comprise an apparatus. The apparatus may comprise a computing apparatus, such as for example, a portable computing device (e.g., smartphone, laptop, tablet) or a desktop computing device (e.g., PC, TV).

In accordance with this aspect of the disclosed technology the apparatus may comprise a communications interface; a display; and one or more computing devices coupled to one or more memory devices, the one or more memory devices containing instructions that cause the one or more processing devices to process input information and health information. For instance, the instructions may cause the one or more processing devices to: obtain input information comprising one or more of text information and image data displayed on the display; obtain health information at a given time marker from a wearable device associated with a user; associate at least one of the text information and image information with the given time marker based on a determination that the received health information is at least at a threshold value; and correlate, using a model, other text information or other image information to the text information or the image information based on the received health information. In accordance with this aspect of the disclosed technology the instructions may cause the one or more processing devices to generate a stress indicator based on a determination that the other text information and other image information are correlated to the text information and the image information associated with the received health information.

In accordance with this aspect of the disclosed technology the one or more instructions may also cause the one or more processing devices to perform one or more of the following operations: classify the text information to produce a first numerical value; determine a topic category associated with the text information to produce a second numerical value; classify the image data to produce a third numerical value; and form a first vector comprising the first, second, and third numerical values and the received health information. In addition, the instructions may cause the one or more processing devices to correlate by searching a vector space having a plurality of vectors using the received health information of the first vector. Further, the instructions may cause the one or more processing devices to classify the text information by classifying the text information using a sentiment classifier. In some examples, an output of the sentiment classifier is mapped to numerical values including the first numerical value. In some examples, the sentiment classifier comprises one of a Support Vector Machine (SVM), a Bayesian classifier or Long Short Term Memory (LSTM) derived model.

In accordance with this aspect of the disclosed technology, image data may comprise video or still image data. Further, the image data is viewable through an application on the apparatus.

In accordance with this aspect of the disclosed technology, health information may comprise one or more of a heart rate, heart rate variability, temperature, stress from EDA activity, user motion, and sleep data.

In accordance with this aspect of the disclosed technology, the stress indicator may comprise a message that notifies the user of the stressor event.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 2E is a schematic diagram of communication between devices according to aspects of this disclosure.

DETAILED DESCRIPTION

Overview

Figure 1:
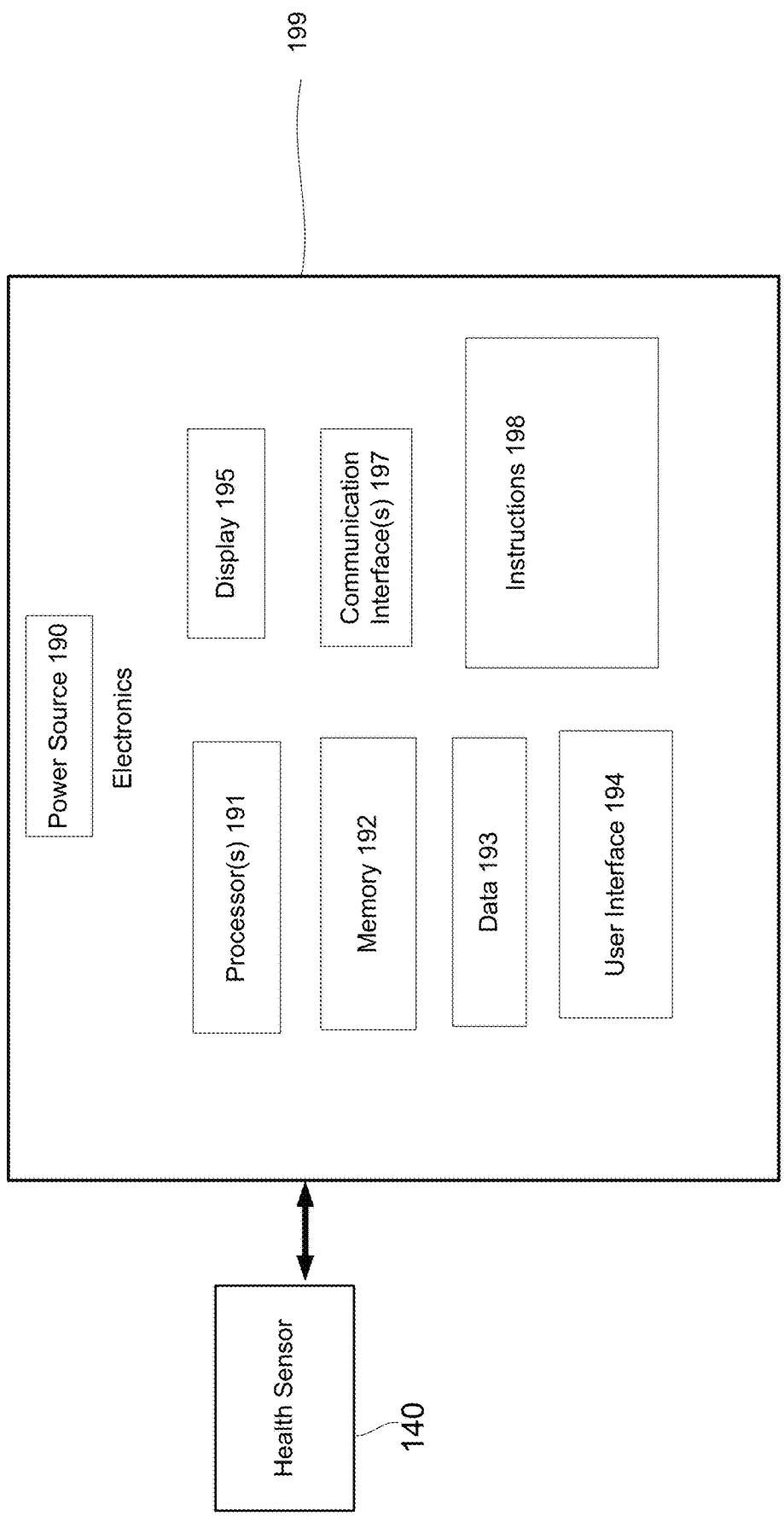
FIG. 1 is a schematic drawing of electronics according to aspects of this disclosure.

This technology relates to techniques for identifying stress related stimuli for a subject or user. More specifically, the technology measures health statistics associated with the subject and detects content viewed by the subject on a device's display. The health statistics and detected content may then be correlated to detect, identify, and track mental stressors for the subject. In addition, the technology may notify the subject of such stressors to potentially reduce the negative impact such stressors may have on the subject's mental and physical health.

Stressor identification and tracking, via one or more computing devices for example, can be used to mitigate stress for a subject. Aspects of the disclosed technology use sentiment analysis and cross device hardware and software signals in a framework to identify, track and notify users or subjects of stressors and thereby provide such subjects with a tool to avoid or mitigate stressful content. This, in turn, should reduce the negative impact on mental and/or physical health such stressors have on subjects.

For example, a wearable device may monitor health related features associated with a subject such as heart rate, oxygen saturation levels, stress from EDA activity, temperature, movement (e.g., steps, distance walked or ran) and sleep data. These features may be provided to a second device, e.g., a smartphone or smart TV, on which the user may view content. When the second device determines that one or more of the health related features meet or exceed a threshold, the second device may determine what on-screen content was being viewed by the subject at the time the threshold was exceeded and notify the user of a stressor event. For instance, if the subject's heart rate exceeds a threshold value (e.g., 80 bpm), the second device may determine the type of content on the user's screen at the time the subject's heart rate exceeded the threshold. In other examples, a combination of signals can be used to determine a threshold value or threshold condition. When the threshold is exceeded, the user may be notified that their heart rate exceeded the threshold and the type of content displayed on screen when the heart rate exceeded the threshold. The type of content may also be tagged within the second device such that when similar content appears on screen, the subject may be notified that such content may be a stressor event for the subject.

Aspects of the disclosed technology uses multiple inputs to estimate how stimuli mentally and physiologically impacts a subject or user. All inputs are processed locally on the subject's device using a model. Input signals may comprise video and imagery viewable to a user via an application (e.g., YouTube and a web browser). Text information viewable via a web browser or a social media application may also serve as inputs but such information is only used for the purposes of the model generating an output that can be read by the user. In addition, model inputs are not shared with an entity that provides this service, e.g., Google, nor any third party. The disclosed technology may be implemented as a separate application on a user device (e.g., Stressor Application) and may only monitor content viewed by the user on applications that are approved (e.g., whitelisted) by the user. For instance, such an application may request from the user which applications should be whitelisted to be used for stressor monitoring and notifications. In addition, over time the user may add or remove whitelisted applications. Further, the stress application may allow for all information generated or related to the application to be deleted or erased, such that the stored information, and any information generated, including trained models, are removed. More generally, an application implementing the feature of the disclosed technology can be configured so the application does not function without usci consent, and all the model and stored information can be deleted without any residue as well as similarly deleting the application.

In addition to inputs from the foregoing applications, the application or model also receives health signals from a wearable device, such as a watch, ring or other device that may detect health related signals. The health related signals may be processed to derive health related parameters or features. Alternatively, the wearable device may derive the health related parameters or features and provide them to the application or model.

These inputs may be provided to a machine learning model running on the user's smartphone or other device. Specifically, whitelisted text data may be used as input to a sentiment classifier. This sentiment classifier may be implemented using a support vector machine (SVM), a long short term memory (LSTM) derived model, or any model capable of text classification. The sentiment classifier may provide discrete outputs such as positive, negative, violent, frightening, verbose, etc. These discrete outputs are mapped to numerical values, e.g., positive—1, negative—2, violent—3, etc., which are more convenient for vectorization.

Whitelisted text data is also fed to a topic modeler. Generally, such a topic modeler may make use of dimensionality reduction, clustering, and automated (or semi-automated) topic tagging. Acceptable algorithms that may be used in this aspect of the technology may include without limitation any one of Linear Discriminant Analysis (LDA), Latent Semantic Analysis (LSA), or Probabilistic LSA (pLSA) topic model approaches. Topic may comprise broad categories such as for example news, technology, sport, etc. Topics may also be more granular such as for example "war news," "crime news," "political news," "space technology,"

"car technology," "food technology," etc. The topic modeler also maps the topics to numerical values for vectorization.

Image and video data is classified based on type and provided as input to the model. For instance, a video of a cat would be tagged as "cat video." A video involving news coverage of a bombing may be tagged "news video" and "bombing." Tags may be mapped to numerical values. For example, news may be mapped to a value of 5, while "cat video" may be mapped to a value of 10.

Health related statistics, features, or parameters, e.g., heart rate data, heart rate variability data, sleep data, etc., are also provided to the model. Such data may be provided from a wearable device as signals or may be derived from signals provided by the wearable device.

The outputs of the sentiment classifier, media modeler, media classifier and health features are vectorized using their numerical values. The numerical values of the sentiment classifier, media modeler, and media classifier are mapped onto the same scale. Each vector's glue is time, e.g., the time at which a specific health signal, text and image occurred are mapped to a vector which then exists in the vector space.

Dimensionality reduction may be applied in the vector space to determine which dimension of the vector, e.g., which of N-dimensions, contributes the most variance. Dimensionality reduction functions to reduce the size of the dataset. In general, an algorithm is run to select a set of principal components to use. For example, a target may be set as an amount of variance to incorporate (e.g., 95%) and then a determination is made as the number of components that are required to get to the target. Examples of dimensionality reduction algorithms that may be used include, for example, Principal Component Analysis (PCA). The principal components may be used to measure the distance metric. A target variance for the data can be set or determined based on defined parameters.

To determine a correlation between specific events that occur in a user's life, such as looking at social media and being stressed, the vector space can be "queried" for a specific test case. For example, if a stressful health signal is detected, the stressor application may query the space for vectors with a similar signal given some error buffer (since it's unlikely the sensor/post-proces sing algorithm will output the same value every time) and look at the density of the vector space around the specific vector "closest" to a query. As one example, vectors which are close in Euclidean distance, or another defined distance metric, can be selected until a certain number of vectors are found, or the closest "n" vectors are found.

A density clustering technique such as DBSCAN may be used to understand if there is a correlation. The densest clusters will likely represent related factors, since the subcomponents are similar resulting in repeated instances of the vectors appearing in the N-dimensional space. A threshold (% or ratio) may be defined before a recommendation may be made to a user or that a trend is detected. This may be a threshold based on the size of a cluster, or based on the size of a cluster relative to other clusters. In some examples, the threshold can be tunable based on user feedback, user sensitivity parameters, or pre-defined sensitivity settings, such as, for example, a range from 0 to 10.

An aspect of the technology is the use of Federated Learning to develop and update models associated with processing the inputs. Federated Learning enables, for example, mobile devices to collaboratively learn a shared prediction model while maintaining the training data locally on the device. As such, in accordance with the disclosed technology, a mobile device may download the shared model from, for example, the cloud. The shared model may then be updated by learning from events that take place on the mobile or other user device. In effect, the original shared model may become more personalized to the user. An anonymized and locally trained model, without underlying user data, on user devices may be saved as updates that are then sent back to the cloud to update the shared model. The updated shared model may then be provided back to individual user devices. Because in a Federated Learning Model environment all the training data remains on each user device, user privacy is ensured.

In another aspect, the model may also receive as input event tagging by a user. For example, when the user is notified of a stressor event, the user may be prompted for input as to their mood, etc. The model may then associate this tag with the event and use it to find similar events in the vector space and apply the tag to those vectors.

By analyzing multiple signals, the present technology allows for more in-depth feedback to a user beyond "your screen time was up this week by X % and your sleep was down by Y %". It allows for providing more specific feedback to a user such as: "Your stress levels tend to increase when you watch action videos on YouTube before bed. To sleep better and feel less stressed, you should not watch videos before bed."

Example Systems

FIG. 1 illustrates additional aspects of electronics 199, which may be used in aspects of the disclosed technology as described in further detail below. Electronics 199 can be any computing device which is capable of performing the steps and algorithms described herein, such as without limitations, cell-phones, tablets, computers, laptops, servers, smart devices, or smart watches. Although the description in FIG. 1 is given with respect to electronics 199, a person of skill in the art should understand that in some examples electronics 199 can be combined or operate collectively with health sensor 140. Illustrated in FIG. 1 is a bidirectional arrow indicating that communication(s) between a health sensor 140 and electronics 199 can occur.

Health sensor 140 can be any device, circuitry, or module which can be used to observe or determine information related to a health state of a user, such as, for example, blood pressure, blood oxygen levels, stress, or other metrics which can be derived from a combination of the exemplary aforementioned metrics. Health sensor equipment, such as an analog front end, photodetectors, accelerometers, or health sensors, such as photoplethysmography sensors, devices, or circuitry. In some examples, a health sensor need not be part of the same device as electronics 199, and can be included in a separate device. It is to be understood that although health sensor 140 is illustrated with a specific configuration, other arrangements of these components are within the scope of this disclosure. In other examples, health sensor 140 can be included or arranged within user devices, such as a mechanical watch, a smart watch, a smart ring, a cell phone, earbud, headphone, armband, or a laptop computer. In other examples, health sensor 140 can be integrated into jewelry, such as a pendant, necklace, bangle, earring, armband, ring, anklet, or other jewelry.

Electronics 199 may contain a power source 190, processor(s) 191, memory 192, data 193, a user interface 194, a display 195, communication interface(s) 197, and instructions 498. The power source may be any suitable power source to generate electricity, such as a battery, a chemical cell, a capacitor, a solar panel, or an inductive charger. Processor(s) 191 may be any conventional processors, such as commercially available microprocessors or application-specific integrated circuits (ASICs); memory, which may store information that is accessible by the processors including instructions that may be executed by the processors, and data. Memory 192 may be of a type of memory operative to store information accessible by the processors, including a non-transitory computer-readable medium, or other medium that stores data that may be read with the aid of an electronic device, such as a hard-drive, memory card, read-only memory ("ROM"), random access memory ("RAM"), optical disks, as well as other write-capable and read-only memories. The subject matter disclosed herein may include different combinations of the foregoing, whereby different portions of the instructions and data are stored on different types of media. Data 193 of electronics 199 may be retrieved, stored or modified by the processors in accordance with the instructions 198. For instance, although the present disclosure is not limited by a particular data structure, data 193 may be stored in computer registers, in a relational database as a table having a plurality of different fields and records, XML documents, or flat files. Data 193 may also be formatted in a computer-readable format such as, but not limited to, binary values, ASCII, or Unicode. Moreover, data 193 may comprise information sufficient to identify the relevant information, such as numbers, descriptive text, proprietary codes, pointers, references to data stored in other memories (including other network locations) or information that is used by a function to calculate the relevant data.

Instructions 198 may control various components and functions of health sensor 140. For example, instructions 198 may be executed to selectively activate light source 110 or process information obtained by photodetector 120. In some examples, algorithms can be included as a subset of or otherwise as part of instructions 198 included in electronics 199.

Instructions 198 can include algorithms to interpret or process information received from the health sensor 140 or from other parts of electronics 199, such as information received through or generated by analyzing health information from health sensor 140, information in data 193, information displayed on display 195, or information processed by processors 191. For example, physical parameters of the user can be extracted or analyzed through algorithms. Without limitation the algorithms could use any or all information about the waveform, such as shape, frequency, or period of a wave, Fourier analysis of the signal, harmonic analysis, pulse width, pulse area, peak to peak interval, pulse interval, intensity or amount of light received by a photodetector, wavelength shift, or derivatives of the signal generated or received by a photodetector of health sensor 140. Other algorithms can be included to calculate absorption of oxygen in oxyhemoglobin and deoxyhemoglobin, heart arrhythmias, heart rate, premature ventricular contractions, missed beats, systolic and diastolic peaks, and large artery stiffness index. In yet other examples, artificial learning or machine learning algorithms can be used in both deterministic and non-deterministic ways to extract information related to a physical condition of a user such as blood pressure and stress levels, from, for example, heart rate variability. PPG can also be used to measure blood pressure by computing the pulse wave velocity between two points on the skin separated by a certain distance. Pulse wave velocity is proportional to blood pressure and that relationship can be used to calculate the blood pressure. In some examples, the algorithms can be modified or use information input by a user into memory of electronics 199 such as the user's weight, height, age, cholesterol, genetic information, body fat percentage, or other physical parameters. In other examples, machine learning algorithms can be used to detect and monitor for known or undetected health conditions, such as an arrhythmia, based on information generated by the photodetectors, health sensors, and/or processors.

Instructions 198 can also include trained machine learning modules which can be used to determine whether a sensor is present or included on a user device.

User interface 194 may be a screen which allows a user to interact with health sensor 140, such as a touch screen or buttons. Display 195 can be an LCD, LED, mobile phone display, electronic ink, or other display to display information about health sensor 140. User interface 194 can allow for both input from a user and output to a user. In some examples, the user interface 194 can be part of electronics 199 or health sensor 140, while in other examples, the user interface can be considered part of a user device. User interface 194 may also comprise devices such as keyboards, etc.

Communication interface(s) 197 can include hardware and software to enable communication of data over standards such as Wi-Fi, Bluetooth, infrared, radio-wave, and/or other analog and digital communication standards. Communication interface(s) 197 allow for electronics 199 to be updated and information generated by health sensor 140 to be shared to other devices. In some examples, communication interface(s) 197 can send historical information stored in memory 192 to another user device for display, storage, or further analysis. In other examples, communication interface(s) 197 can send the signal generated by the photodetector to another user device in real-time or afterwards for display on that device. In other examples, communication interface(s) 197 can communicate to another PPG module. Communication interface(s) 197 can include bluetooth, Wi-Fi, Gazelle, ANT, LTE, WCDMA, or other wireless protocols and hardware which enable communication between two devices.

Figure 2A:
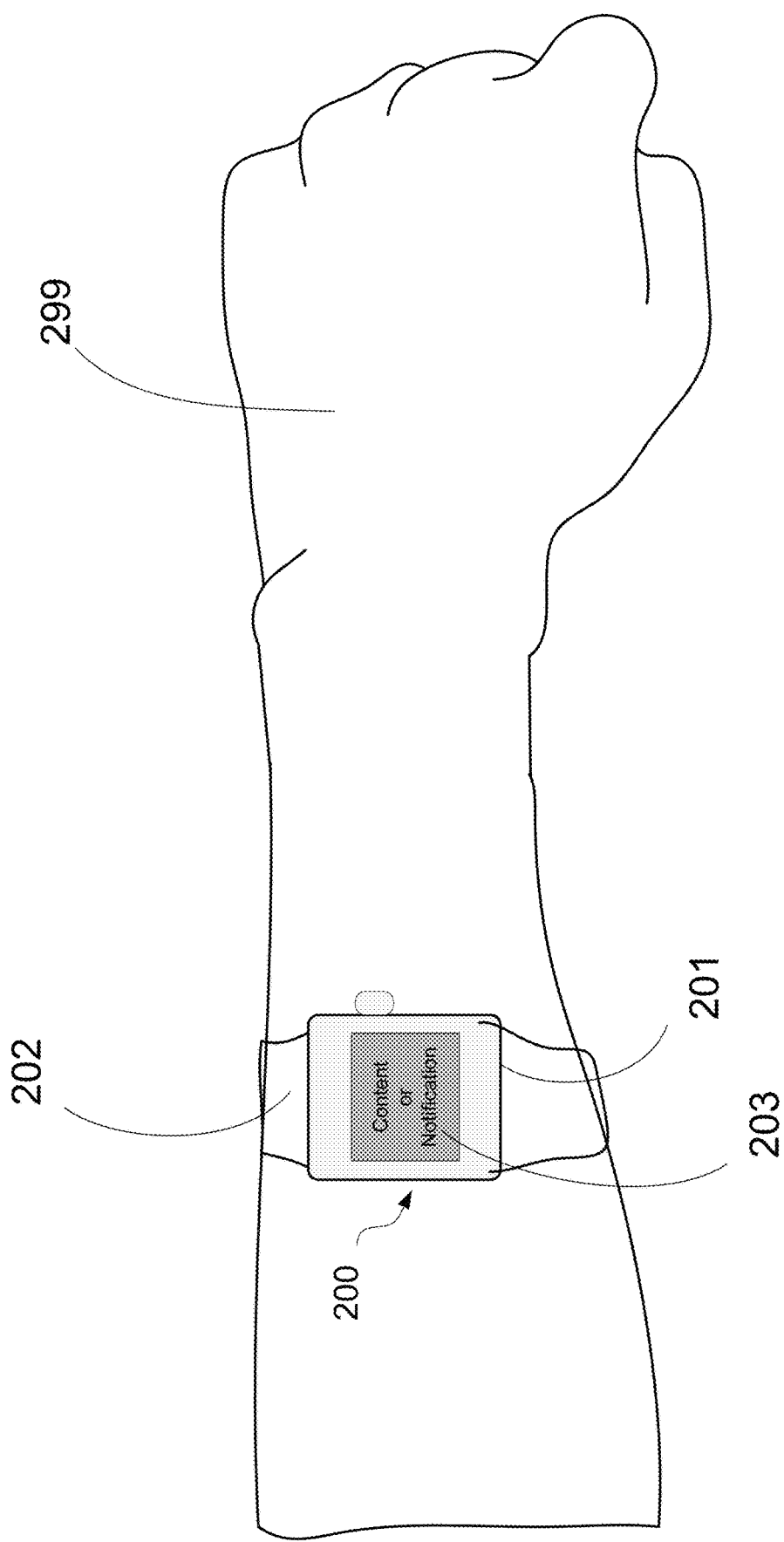
FIG. 2A is an illustration of a wearable user device capable of PPG functions according to aspects of this disclosure.

FIG. 2A illustrates a user device, 200, which can be worn by a user, such as user 299. The user device can include a housing 201, and a strap 202. Housing 201 can have components such as a back portion, which will contact the skin of user 299. The back portion can contain an optically transparent portion which allows light to pass through the back portion. For example, light can be generated from other components contained within housing 201, such as a light source. User device 200 and housing 201 can also have a user interface which allows user 299 to interact and view information from user device 200. The user interface can be part of a touchscreen or other device. Additional components which can be included in user device 200 or in housing 201 are further described above with reference to FIG. 1. The housing can further be of an appropriate thickness to include the components described in FIG. 1. Strap 202 can be a strap to hold the user device on a user, such as one made from metal, leather, cloth, or other material. User device 200 can contain a health sensor module 140 to perform health sensing functions.

Although a smartwatch is illustrated as user device 200, a person of skill in the art will appreciate that user device 200 can take on a variety of forms. User device 200 can also be a health sensor, an earbud or earplug, headphone, or other wearable electronics, a ring, a bangle, an anklet, necklace, or other piece of jewelry. A notification on user device 200 can be a visual notification, such as on display 203 of the user device while in other examples, according to the capabilities of the user device, other notifications can be given such as through a vibration, an audio alert, a beep, a flash, or other notification.

Figure 2B:
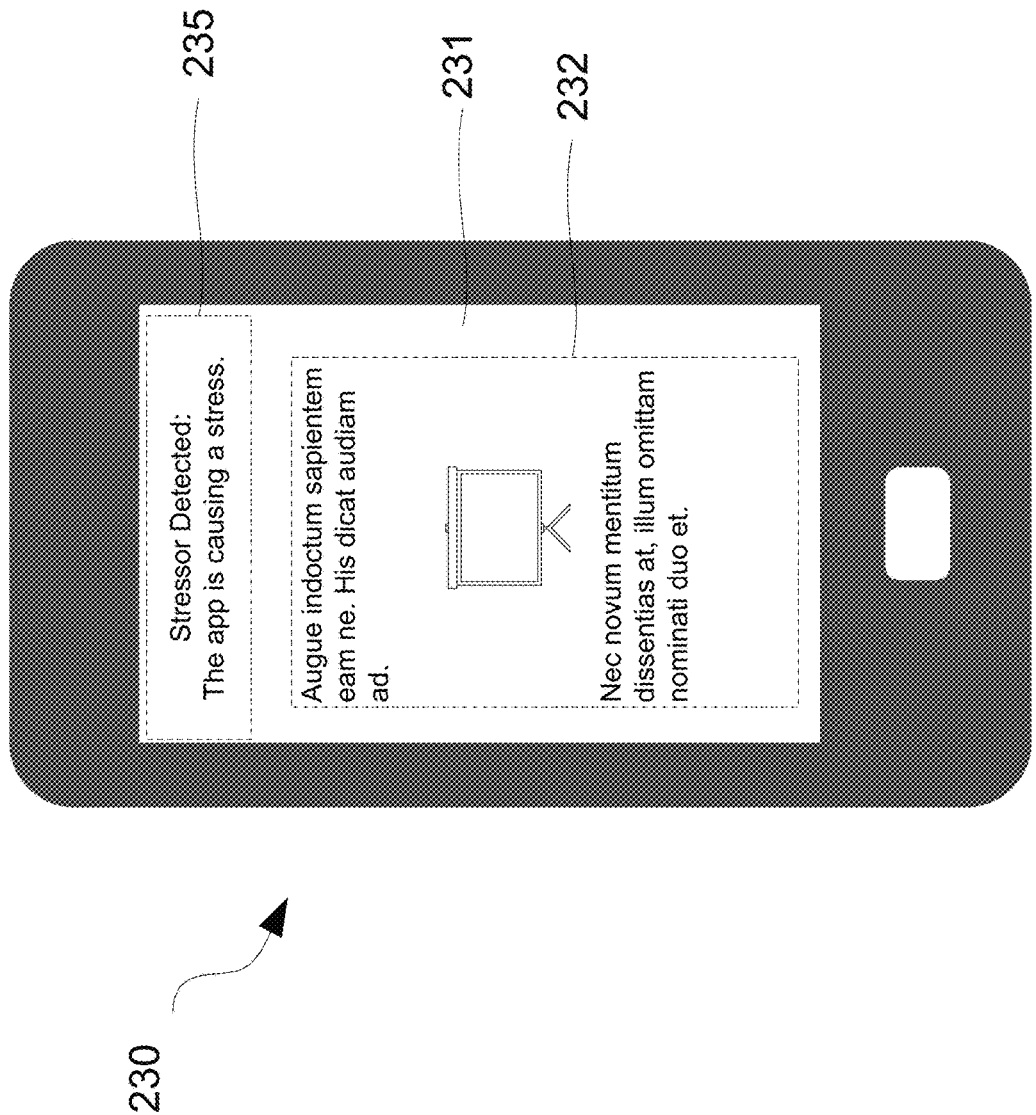
FIG. 2B is a diagram of user interfaces according to aspects of this disclosure.

FIG. 2B illustrates a user device 230. User device 230 can contain various components described with reference to FIG. 1 in electronics 199, which are omitted from FIG. 2B for simplicity. Illustrated in FIG. 2B is display 231 displaying content 232. Content 232 can include textual content, visual data, such as images or videos, as well as meta-data which may or may not be displayed on user device 230.

Superimposed on the content 232 is notification 235. Notification 235 can be displayed when the content displayed is causing a threshold related to the user's health to be exceeded. In other examples, notification 235 can be displayed preemptively when content 232 is first loaded or about to be loaded onto user device 230 based on the information contained therein. In some examples, the content can be "paused" before being loaded to prevent a potentially stressful event to occur. Further, a summary of the type of content can be provided to a user for the user to determine if the user would like to continue to view the content.

Figure 2D:
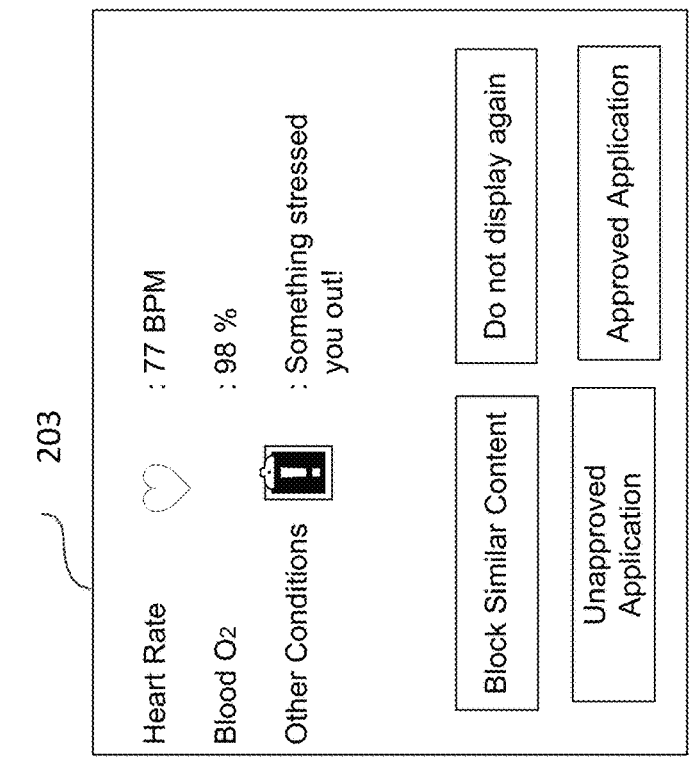
FIG. 2D is a schematic diagram of communication between devices according to aspects of this disclosure.
Figure 2C:
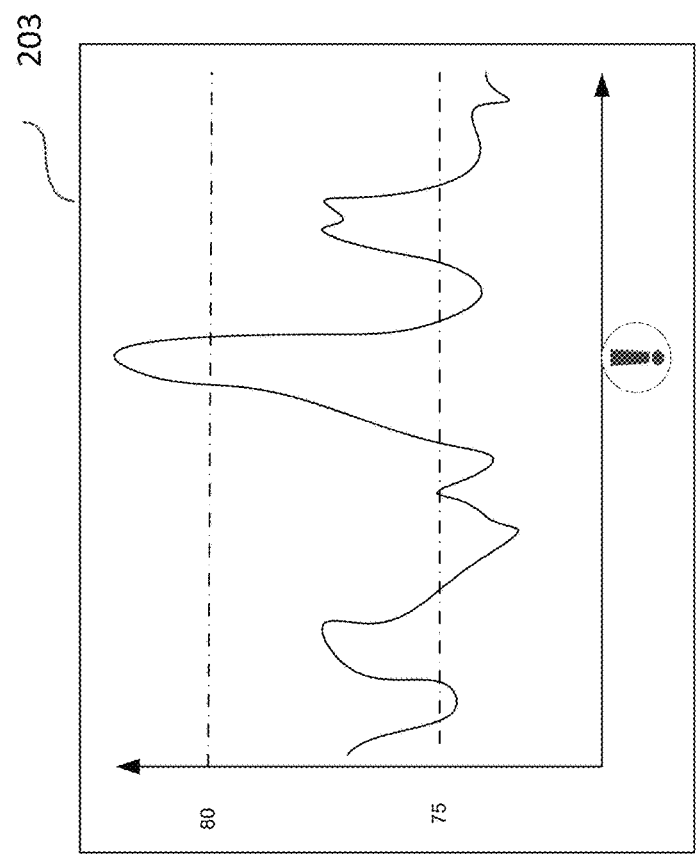
FIG. 2C is a diagram of user interfaces according to aspects of this disclosure.

FIG. 2C and FIG. 2D illustrate example formats of displaying information about a physical condition of a user on a display 203 or display 231, which can be similar to display 195 described above. FIG. 2C illustrates a graph of the heart rate of a user of a device, such as device 200. This graphical view can be updated in real time to display a trailing number of seconds of the heartbeat of the user. In some examples, in "real time" or "real-time" can mean the execution of data instructions, or algorithms in a short time period, which can provide near-instantaneous output to a user or user device. The heartbeat being displayed can be obtained from the methods described herein. A notification of when the user's heartbeat is higher than a certain threshold, such as 80 beats per minute can be indicated with an interactable exclamation mark "!" or other notification. The notification may be associated with content which was displayed on the user device.

FIG. 2D illustrates displaying information about a physical condition of a user in a textual format. For example, FIG. 2D illustrates the current heart rate in beats-per-minute (BPM), the current blood oxygen saturation level, and any other conditions that may be of value to the user, such as an arrhythmia. Although the examples given are for cardiovascular conditions, other aspects of the heart can be monitored.

FIG. 2D also illustrates other options, such as the ability to block the content/application which is causing a particular stress (Unapproved Application), to approve the content/application (Approved Application), to not display the notification again, or to block similar content/applications. Although information is displayed in a visual format, in other examples, the information may be provided through an auditory method. Information being displayed in FIG. 2D can be derived from the methods described herein.

FIG. 2E illustrates communication between two user devices, user device 200 and user device 290 worn by user 299. In this instance, user device 290 is an earbud. Although the same reference numerals are used for the devices in FIG. 2E as the devices in FIGS. 2A-2B, these devices need not be the same devices. In other examples, user device 290 can be headphones, a pendant, or other device containing a health sensor, such as health sensor 140. As explained further below, each user device can compute or derive health related information, and a combination of the information can be used when determining thresholds for user's stress. For example, one device may determine heart rate while another determines blood pressure or blood oxygen level. In some examples, a device not containing a health sensor, such as smartphone 291 can receive health related information from user device 200 and user device 290 and combine the two estimates together.

Figure 2F:
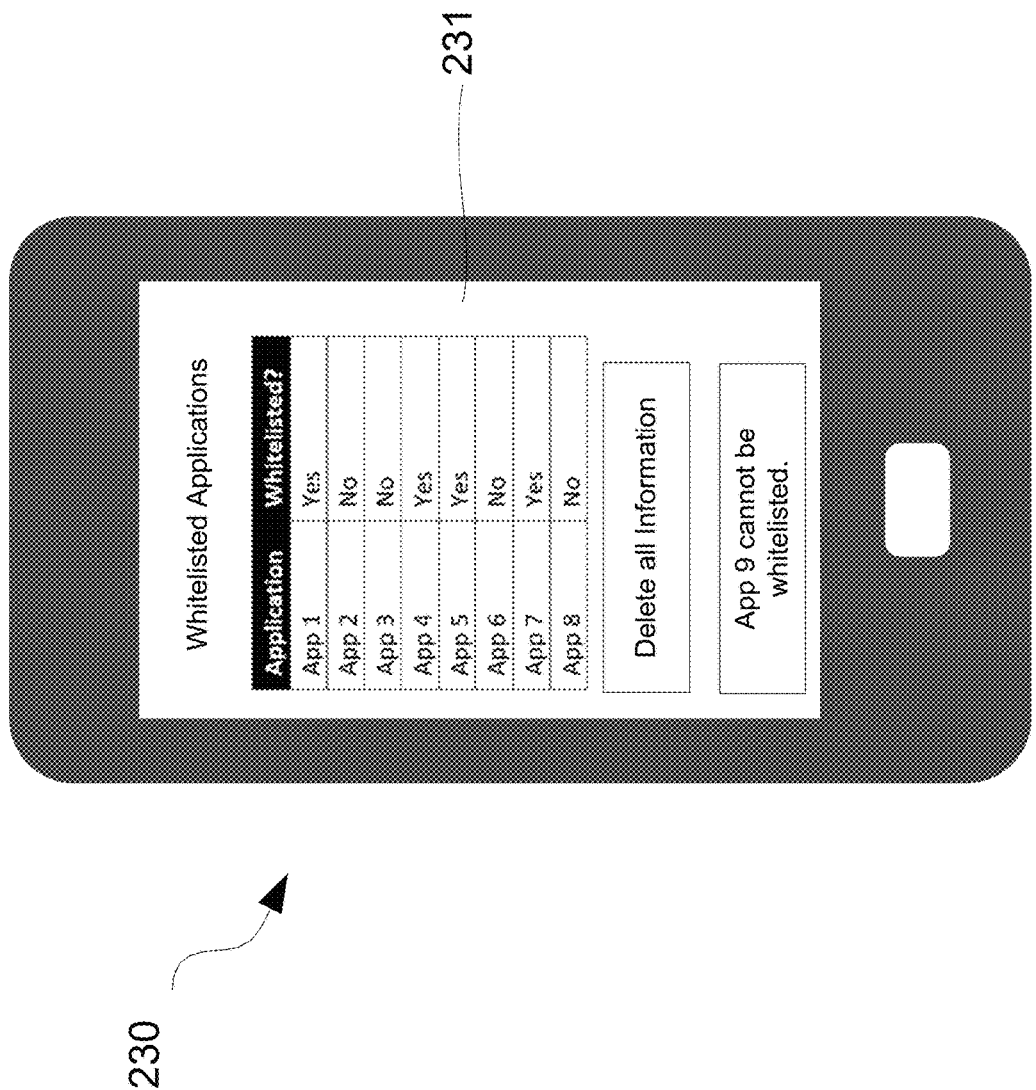
FIG. 2F is a schematic diagram of communication between two PPG modules according to aspects of this disclosure.

FIG. 2F illustrates an example of a user interface where a user can determine or choose which applications she wishes to approve for analyses for stressors, the analysis of which can occur locally, anonymously, and privately on the user device. An application which has been approved or whitelisted can be analyzed by the systems, methods, and devices described herein. In some examples, the whitelisted applications can be generated automatically based on user preferences or default suggestions. In other cases, applications which contain a certain type of data can not be whitelisted based on the type of content the application contains, such as for example, voice data, email data, or data related to a confidential or private application.

Example Methods

As explained below, the following techniques or methods can be used to analyze approved or whitelisted data or applications for local stressors.

Figure 3:
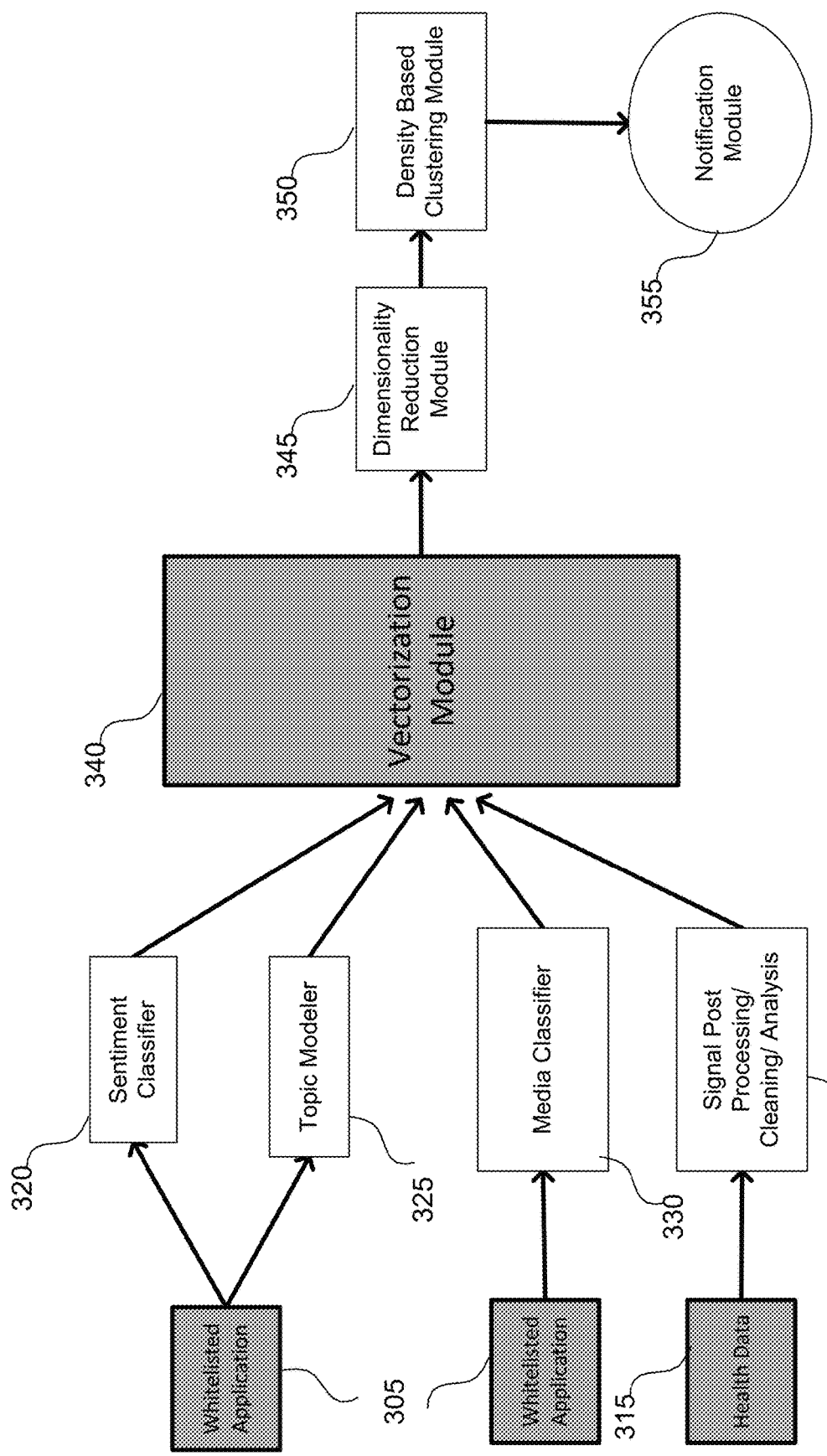
FIG. 3 is a flowchart of an example method according to aspects of this disclosure.

FIG. 3 illustrates an example schematic view of architecture 300. FIG. 3 illustrates an example of how multiple inputs can be used to estimate how stimuli mentally and physiologically impacts a subject or user. All inputs are processed locally on the subject's device using a model. Input signals may comprise video and imagery viewable to a user via an application (e.g., YouTube and a web browser). Text information viewable via a web browser or a social media application may also serve as inputs.

Illustrated in FIG. 3 is approved application 305. An approved application 305 may include any application that processes data on a device, such as the devices discussed above. Examples of such applications include YouTube, web browsers, newspapers, or any other application that a user approves to be monitored for stressor content. In this regard, aspects of the disclosed technology may be implemented as an application that monitors screen displays for data or receives data from other applications, processes the data it receives and produces stressor indicators.

In this regard, processing may be implemented using the elements, modules or blocks shown in FIG. 3. Further in this regard, sentiment classifier 320 can include one or more models which can be used to analyze text data. In some examples, sentiment classifier 320 can include a Bayesian classifier, a long short-term memory model, an artificial recurrent network, or a support vector machine model. Other models or techniques which can analyze textual information to provide an output can be used. Sentiment classifier may provide a discrete output to the textual input, such as, for example, positive or negative. Other examples of an output can include additional categorizations, such as violent, frightening, verbose, positive, uplifting. The categorical values can be associated with or mapped to numerical values for use in by vectorization module 340. For example, a scale may be applied to possible outputs of the sentiment classifier such that a violent output is given a numerical value on the scale, frightening another, verbose another, etc. As a specific example, assuming a scale of 1 to 100, violent text may be assigned a numerical value of 90, while uplifting text a value of 10. These values are then outputted to the vectorization module, which includes them in a vector along with other numerical values it receives from other classifiers or modelers. While numerical values may be used, other output values may be output including text, etc.

Topic modeler 325 can also receive textual information from the whitelisted application simultaneously, in real time, or in near-time as sentiment classifier 320. Models or techniques which can take as an input textual information and provided as an output a value, such as "technology," "sports," "news," "food" can be used. For example, models which use dimensionality reduction, clustering, or automated or semi-automated tagging or topics can be used. Specific examples can include Linear Discriminant Analysis (LDA), latent semantic analysis (LSA), probabilistic latent semantic analysis (pLSA) models. In some examples, the model used can include information which has been tagged using a human-assisted method. Topic may comprise broad categories such as for example news, technology, sport, etc. Topics may also be more granular such as for example "war news," "crime news," "political news," "space technology," "car technology," "food technology," etc. Topic modeler 325 may also be configured to output a numerical value to allow for easier vectorization.

Media classifier 330 can include one or more models which can take a video, or meta-data related to a video, or other media, and classify the model. For example, a video of a dog could be tagged as "dog video" by media classifier 330. In some examples, a more granular tagging could be used. For instance, a dog video involving a Dalmatian may be tagged as "dog" and "dalmation" while a dog video involving a Shiba Inu could be tagged as "dog" and "Shiba." These values can be mapped to arbitrary numerical values in one-to-one correspondence with the tags.

The individual models (sentiment classification, topic modeler, etc.) may be pre-trained on pre-existing datasets. The trained models may then be supplied as part of the stressor application through, for example, a "copy and paste" function. This functionality may be implemented using transfer learning techniques used, for example, in deep learning applications.

Module 335 can perform signal post processing, cleaning of a signal, or analysis of information, a signal, or other data related to health data 315. Signal post processing may be performed, for example, to filter out noise, remove artifacts or remove false signals. Health data 315 can be obtained from, for example, health sensor 140. Health related statistics, features, or parameters, e.g., heart rate data, heart rate variability data, sleep data, PPG data, etc., are also provided to the model. Such data may be provided from a wearable device as signals or may be derived from signals provided by the wearable device. In some examples, module 335 can include additional specialized information for analysis depending on the type of health data 315 available. In some examples, a stress signal may be provided by an EDA sensor on the wearable, or from some combination of cameras that can infer mood and stress.

Vectorization module 340 can "vectorize" the information obtained from the modules described above. The outputs of sentiment classifier 320, media modeler 325, media classifier 330 and module 335 are vectorized using their numerical values. The numerical values obtained can be mapped onto the same scale. In some examples, a vector can be created or specified by a time value, such as the time at which the specific information forming the numerical values are being mapped into a vector. In this manner, each vector can correspond to or be uniquely related to a specific time value. Although examples are given with a specific number of values, any vector with "N" dimensions can be generated using "N" or more inputs. Although vectorization module 340 is described as a vector, a person of skill in the art will appreciate that a n-tuple or other mathematical formulation of the data can be used.

Dimensionality reduction module 345 can reduce the "distance" between the vectors which are generated. Dimensionality reduction module 345 can include any dimensionality reduction technique. As one example, principal component analysis can be used to analyze or identify which dimensions of the "N" dimensional vectors most contributes to the variance. Additional examples and details of dimensionality reduction are provided with respect to FIG. 4. In some examples stress can be measured or derived from an EDA sensor on a wearable while in other examples, stress can be a metric generated from a combination of data from sensors, e.g., cameras which can infer mood or stress.

Density based clustering module 350 can use specific test cases where a stressful health signal or indicator is present and query the vector with a similar signal or signature (e.g., within a specific error range) to look at the density of the vector space around the specific vector which is "close" or similar to the queried vector. Clusters which are the densest will likely indicate that the factors are related as the subcomponents are similar resulting in repeated instances of the vectors appearing in the N-dimensional space. For example, for some stress level, denoted by 'S', all vectors which contain S larger than an established value may exhibit similar or the same things, such as a level of noise or an amount of media consumed. In some examples, a certain threshold, such as measured by a percentage or ratio, must be met before a cluster is considered to be detected or valid, or used as a trigger for a certain condition. In some examples, additional threshold values can be added, such as the size of the cluster, the relative size of the clusters, or a global optimization of the largest or most impactful k-clusters.

Notification module 355 can provide a user notification related to a stressful trigger or event upon a model or algorithm determining that the information analyzed is likely to correspond to a stressful event. In some examples, the user notification can be similar to notification 235 given with respect to FIG. 2B. In some examples, the notification can be interactive and allow a user to provide additional information, such as whether he or she actually feels stressed, describe a mood (e.g., anxious, excited, positive, negative), or provide whether he or she wants to see more or less frequent or tailored notifications. For example, this information can be used to provide more tailored recommendations. As one specific example, after describing a mood, the information can be used to retrain or customize models further to better or more granularly classify a user's mood.

In some examples, other information can be provided by notification module 355 after an event occurs. For instance, a user may have been exposed to a particular type of content, which may be correlated with a particular health condition, such as for example, a lack of deep sleep or a smaller number of hours slept than usual. Notification module 355 can also provide summary information after stressful events, e.g., not in real time, such as the end of a day or end of a week to allow a user to better understand the impact of a particular type of content. In some examples, notification module 355 can also correlate particular applications, topics, or types of media to a particular effect, such as the viewing of violent videos leading to more sleep or viewing of anxious videos to an overall elevated heart rate. In other examples, the techniques described herein can also adjust for a change in the "baseline" health information of a user, such as for example, when heart rate is elevated when no content is being read. As one example, if a user's heart rate is elevated at a particular time of day, that information may be correlated to a particular event (e.g., drinking coffee) can be used when making determinations by notification module 355.

In some examples, notification module 355 can provide a notification upon determining that the data provided indicates stress above a predetermined threshold. Notification module 355 can perform steps described herein to generate a notification, including those described with respect to FIG. 4.

In some examples, the classifier, model and/or module components described with respect to FIG. 3 can be updated. However, any update of the components described need not involve identification of personalized or identifiable data related to a user. For example, a media classifier may classify a video involving any animal as "animal" while after an update, if the video included a dog, a more granular or updated classification can be obtained, such as "dog." Such updates may occur via the Federated Learning techniques discussed above. In this way, the local processing that takes place on an individual user device may be made more granular or more accurate based on an updated model, e.g., topic modeler, sentiment, or media classifier.

As shown in FIG. 3, processing involves obtaining information about health related parameters or features of user, and information viewed (e.g., video, image) and/or read (e.g., text) by a device used by the user, e.g., a device having the electronic components discussed in relation to FIG. 1. Video and/or image data is received at media classifier 330 where it is classified in accordance with one or more of the criteria discussed above or other criteria defined by a user or the system. Media classifier 330 makes available one or more classification values, e.g., numerical values, it determines for output to the vectorization module.

Textual information associated with image and/or text is provided to sentiment classifier 320 and topic modeler 325. In this example, the information to be processed includes text and video/image. However, in other examples the information may include either type of information. For example, the information being read by a user might be a newspaper article without any images or text. Conversely, the information may include images in an online photo album, which would not call for processing by sentiment classifier 320. Sentiment classifier 325 and topic modeler 325 each output values based on the sentiment and topic analysis performed on the textual information. These output values may be numerical values, which may be more convenient for vectorization.

Signal post processing block 335 makes available health related metrics, e.g., heart rate, heart rate variability, etc., to vectorization module 340. This output may also include a time value that indicates when the health related metrics were captured. The timing component may be used by the vectorization module 340 to determine which of the values it receives from the classifiers and modelers to include in a given vector. More specifically, as a health related metric, such as heart rate, is correlated with the outputs of the classifiers and modelers in determining stressors, it is necessary to tie the timing of a given health metric used as threshold with the time at which content was viewed or received as stimuli by the user. As discussed above, a stressor event may be determined in relation to a user's heart rate exceeding a threshold. In some examples, a stressor event may be determined based on a combination of signals (e.g., EDA monitoring and a HR jump).

In accordance with an aspect of the disclosed technology, the time at which the threshold value is exceeded may be used as the "glue" for vectorization. More specifically, the output values of classifiers 320, 335 and modeler 320 at the time at which the threshold value was exceeded are used to create a vector that is further processed in modules 345 and 350 to provide a stressor indicator or notification.

The vectorization module 340 obtains the numerical values generated from the classifiers 320 and 330, modeler 325 and post processing block 335 and derives a vector that includes the values corresponding to the time a threshold was exceeded or met. This vector is then used to query the vector space for information correlating to, for example, the health metric value of the vector. For example, if a threshold is set based on a heart rate of 90, and a heart rate of 130 is detected while a user is watching a horror movie, a vector would be created that indicates at least a heart rate of 130, the image or multiple images associated with the time the heart rate was at 130. This vector may then be used to find other vectors that are close to the vector used in the query. Closeness may be determined based on, for example, heart rate or value associated with the image, or in some instances the type of image (e.g., based on tagging by the user). Closeness may also be determined based on heart rates with values close to the heart rate value in the query.

As shown in FIG. 3, after dimensionality reduction 345 and clustering 350, notification is provided to a user via notification module 355. Examples of notifications include those shown as examples in FIG. 2D, e.g., Something Stressed You Out. Other notifications may include identification of the content detected as a possible stressor, statistics relating to the content such as a number of prior instances that the same or related stressor has occurred, the heart rate associated with prior instances, etc. In addition, as shown on FIG. 2D, a user may be given the option to block similar content.

Figure 4:
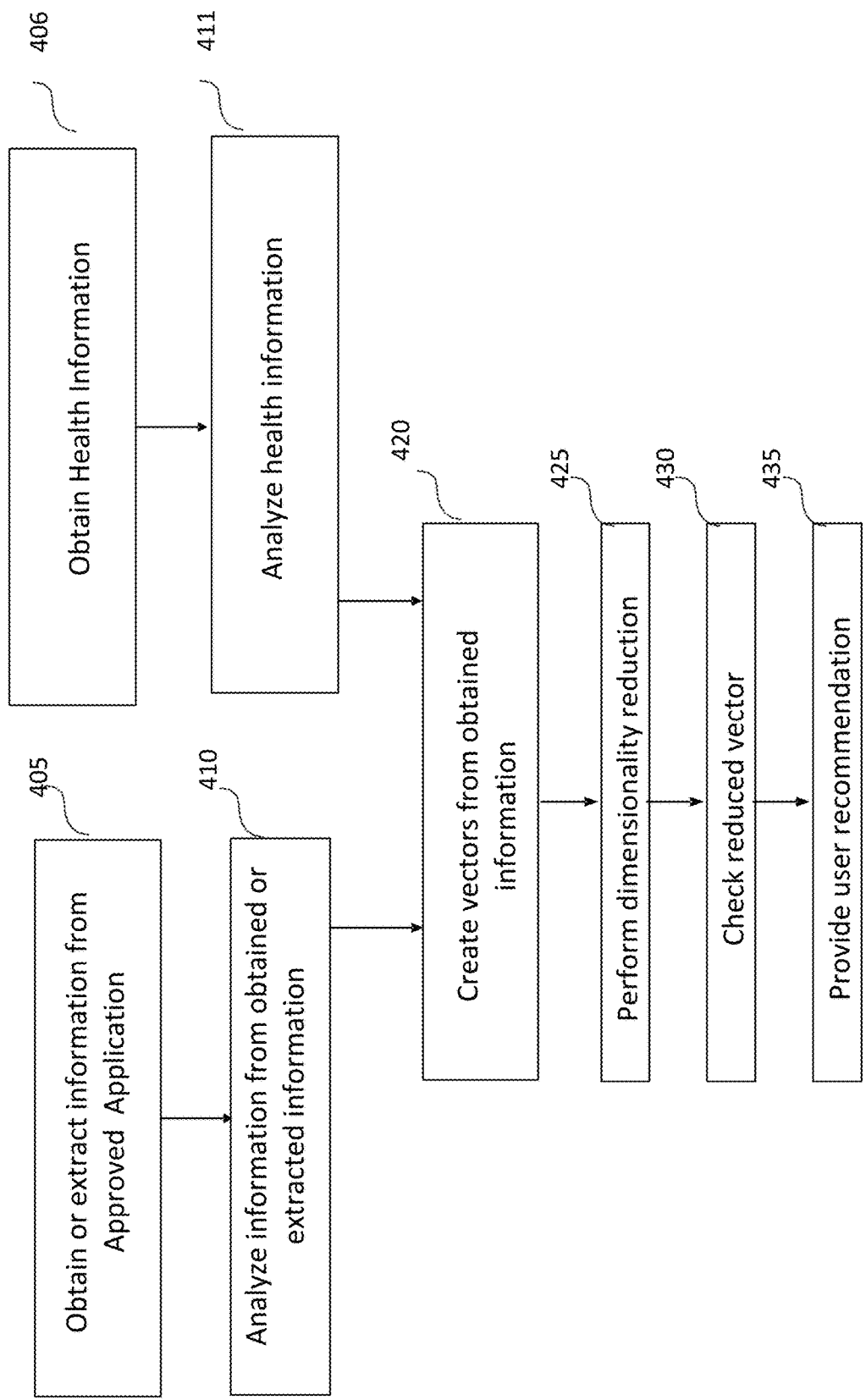
FIG. 4 is a flowchart of an example method according to aspects of this disclosure.

FIG. 4 illustrates method 400 related to aspects of the disclosed technology.

At block 405, information related to a whitelisted application can be obtained or extracted. This information can include visual, textual, audio, meta-data, or other information. This information can be obtained based on user preferences. In some examples, only a subset of information from a whitelisted application can be obtained, such as for example, only textual data but not visual data.

At block 406, health information related to a user of a device, using a whitelisted application, can be obtained. In some examples, this information can be obtained in real-time or near-real time with block 405. In some examples, health information can be obtained from multiple devices, which can be aggregated to provide a more sophisticated analysis.

At block 410, information obtained at block 405 can be analyzed. In some examples, modules, techniques, classifiers, or models described with respect to FIG. 3 can be used for analysis. In some examples, the information can be analyzed or transformed to output a numerical value related to the obtained or extracted information. This can include and is not limited to textual analysis, media classification, sentiment classification, and topic modeling.

At block 411, the health information obtained at block 406 can be analyzed. Techniques described herein can be used without limitation to analyze the information in block 406. In some examples, the health information can be analyzed or transformed to output one or more numerical values related to the obtained health information. Techniques for analysis of health information are provided herein.

At block 420, the information obtained, transformed, or analyzed in blocks 405-411 can be vectorized by a vectorization module, such as vectorization module 340. The vector can be normalized before being processed. In some examples, the vector can be an n-tuple based on n inputs to the vector.

At block 425, dimensionality reduction can be performed. Dimensionality reduction can involve techniques including principal component analysis on the vector space containing vectors related to stress and application data. Principal component analysis is the process or method of determining or computing principal components within a or collection of data points. The principal components of a collection of points within a coordinate space or vector space can be a set of orthogonal vectors which form an orthogonal basis for the set of data. In some examples, the most relevant or important vectors are kept and the rest are discarded. For example, a threshold can be set for the amount of variance which is desired to be represented and captured with the principal components. In this manner, principal component analysis can preserve the desired number of principal components to simplify the number of components being analyzed and increase computational efficiency while preserving the variation of the data within an acceptable or pre-defined level. Principal components, once determined, can be used to measure a distance metric between vectors or data points within the vector space. Although the aforementioned description is provided using principal component analysis, other dimensionality reduction techniques can be used to simplify the obtained data or vectors.

At block 430, density based clustering or other clustering techniques can be performed or used to identify clusters or features within data. Clustering is a method or technique in which clusters can be identified within a set of data. Clusters can be separated from sparser noise surrounding the identified clusters. These clusters can be saved or extracted for classifying future or new data. Any clustering technique can be used within block 430. DBSCAN or defined distance scanning is a technique which can use a specified search distance to identify potential clusters. Other variations can include self-adjusting scanning or HDBSCAN techniques. This range can vary the search distance to allow a range of distances to be used when separating or identifying clusters of varying densities from sparser noise. Multi-scale or OPTICS methods or algorithms can be used. OPTICS algorithms use the distance between neighboring features to determine a reachability plot, which can then be used to separate clusters. The algorithm can be more computationally intensive but provides flexibility in fine-tuning clusters. Other clustering techniques can include machine learning based clustering techniques. In some examples, clustering techniques can generate a model which can be queried to classify an obtained datapoint. In some examples, the obtained datapoint can be added to the model after it is classified or analyzed, and increase the robustness of the model.

At block 435, a user recommendation can be made if a threshold is exceeded. An obtained vector, in real time or near real time, can be analyzed using a proximity approach to see if the vector is close to vectors which are closely clustered and meet a threshold of being stressful. In other examples, the threshold can be adjusted based on user preferences or parameters. In some examples, user data can be matched or classified to an identified cluster (as described, for example, in block 430) to analyze the user data and determine if it corresponds to a stressful event.

Additional steps can be performed in conjunction with or substituted in method 400. For instance, in some examples, one or more models obtained can be updated. In some examples, the models can be updated through models updated using federated learning (FL) techniques. FL can safeguard privacy by eliminating the requirement of needing specific, individual, or sensitive data in training a global model by using securely encoded model updates instead of the sensitive data. In this manner, federal learning can mitigate privacy risks which can be present in creating machine learning models. Further, federal learning can allow for a reduced computational cost in training models. FL techniques can enable models to be trained on individual devices and only provide updates to the model periodically with the global model. The global model can be retrained based on the provided updates.

In some examples, health data within a predetermined time frame from the future can be analyzed with respect to information from whitelisted applications. For example, if an individual is sleepless a few hours after watching a particular type of content or using a particular application, that health information can be analyzed with respect to content viewed within, for example, the last 24 or 48 hours.

Example Machine Learning, Statistical, Probabilistic, and Model Creation Methods In some examples, one or more of the following techniques can be used as part of the disclosed technology.

In some examples, probabilistic methods can be used. For example, a gaussian mixture model can be used. Gaussian mixture models are a probabilistic model for representing normally distributed subpopulations within an overall population. In a Gaussian mixture model, it is not required that an observed set of data should characterize or state which subpopulation a particular observation within the distribution belongs to.

Example machine learning techniques which can be used include the following. In some examples, a mix of supervised learning techniques and unsupervised learning techniques can be used.

In some examples, generative adversarial networks can be used to predict or detect network anomalies. Generative adversarial networks use two networks, one adversarial and one generative, in an attempt to fool the adversarial network by objects generated by the generative network.

In some examples, clustering methods can be used to cluster inputs, network parameters, trained models, or virtual machines. Clustering methods can be used in real time to classify and match models or groups of models with particular criteria. Clustering can be an unsupervised machine learning technique in which the algorithm can define the output. One example clustering method is "K_Means" where K represents the number of clusters that the user can choose to create. Various techniques exist for choosing the value of K, such as for example, the elbow method.

Some other examples of techniques include dimensionality reduction. Dimensionality reduction can be used to remove the amount of information which is least impactful or statistically least significant. In networks, where a large amount of data is generated, and many types of data can be observed, dimensionality reduction can be used in conjunction with any of the techniques described herein. One example dimensionality reduction method is principle component analysis (PCA). PCA can be used to reduce the dimensions or number of variables of a "space" by finding new vectors which can maximize the linear variation of the data. PCA allows the amount of information lost to also be observed and for adjustments in the new vectors chosen to be made. Another example technique is t-Stochastic Neighbor Embedding (t-SNE).

Ensemble methods can be used, which primarily use the idea of combining several predictive models, which can be supervised ML or unsupervised ML to get higher quality predictions than each of the models could provide on their own. As one example, random forest algorithms.

Neural networks and deep learning techniques can also be used for the techniques described above. Neural networks generally attempt to replicate the behavior of biological brains in turning connections between an input and output "on" or "off" in an attempt to maximize a chosen objective.

While this disclosure contains many specific implementation details, these should not be construed as limitations on the scope of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Aspects of the disclosed technology can include any combination of the following features and sub-features:

F1. A method for determining health stressors, comprising:
  receiving input information comprising one or more of text information displayed on a user device of a user and image data displayed on the user device;
  receiving health information at a given time marker from a wearable device associated with the user;
  associating at least one of the text information and image information with the given time marker based on a determination that the received health information is at least a threshold value;
  correlating, using a model, other text information or other image information to the text information or the image information based on the received health information; and
  generating a stress indicator based on a determination that the other text information and other image information are correlated to the text information and the image information associated with the received health information.

F2. The method of F1, comprising one or more of the following steps:
  classifying the text information to produce a first numerical value;
  determining a topic category associated with the text information to produce a second numerical value;
  classifying the image data to produce a third numerical value; and
  forming a first vector comprising the first, second, and third numerical values and the received health information.

F3. The method of any one of F1 and F2, wherein correlating comprises searching a vector space having a plurality of vectors using the received health information of the first vector.

F4. The method of any one of F1 through F3, wherein classifying the text information comprises classifying the text information using a sentiment classifier.

F5. The method of any one of F1 through F4, wherein an output of the sentiment classifier is mapped to numerical values including the first numerical value.

F6. The method of any one of F1 through F5, wherein the sentiment classifier comprises one of a Support Vector Machine (SVM), a Bayesian classifier or Long Short Term Memory (LSTM) derived model.

F7. The method of any one of F1 through F6, wherein image data comprises video or still image data.

F8. The method of any one of F1 through F7, wherein the image data is viewable through an application on the user device.

F9. The method of any one of F1 through F8, wherein health information comprises one or more of a heart rate, heart rate variability, temperature, stress from EDA activity, user motion, and sleep data.

F10. The method of any one of F1 through F9, wherein the stress indicator comprises a message that notifies the user of the stressor event.

F11. An apparatus, comprising:
  a communications interface;
  a display; and
  one or more computing devices coupled to one or more memory devices, the one or more memory devices containing instructions that cause the one or more processing devices to:
    obtain input information comprising one or more of text information and image data displayed on the display;
    obtain health information at a given time marker from a wearable device associated with a user;
    associate at least one of the text information and image information with the given time marker based on a determination that the received health information is at least at a threshold value;
    correlate, using a model, other text information or other image information to the text information or the image information based on the received health information; and
    generate a stress indicator based on a determination that the other text information and other image information are correlated to the text information and the image information associated with the received health information.

F12. The apparatus of claim F11, the one or more instructions cause the one or more processing devices to do one or more of the following operations:
  classify the text information to produce a first numerical value;
  determine a topic category associated with the text information to produce a second numerical value;

classify the image data to produce a third numerical value; and
form a first vector comprising the first, second, and third numerical values and the received health information.

F13. The apparatus of any one of F11 through F12, wherein the instructions cause the one or more processing devices to correlate by searching a vector space having a plurality of vectors using the received health information of the first vector.

F14. The apparatus of any one of F11 through F13, wherein the instructions cause the one or more processing devices to classify the text information by classifying the text information using a sentiment classifier.

F15. The apparatus of any one of F11 through F14, wherein an output of the sentiment classifier is mapped to numerical values including the first numerical value.

F16. The apparatus of any one of F11 through F15, wherein the sentiment classifier comprises one of a Support Vector Machine (SVM), a Bayesian classifier or Long Short Term Memory (LSTM) derived model.

F17. The apparatus of any one of F11 through F16, wherein image data comprises video or still image data.

F18. The apparatus of any one of F11 through F17, wherein the image data is viewable through an application on the apparatus.

F19. The apparatus of any one of F11 through F18, wherein health information comprises one or more of a heart rate, heart rate variability, temperature, stress from EDA activity, user motion, and sleep data.

F20. The apparatus of any one of F11 through F19, wherein the stress indicator comprises a message that notifies the user of the stressor event.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

The invention claimed is:

1. A method for determining health stressors, comprising:
    displaying, by one or more processors, one or more of text information and image information on a user device of a user;
    receiving, by the one or more processors, health information at a given time marker from a wearable device associated with the user during displaying of the one or more of text information and image information;
    associating, by the one or more processors, at least one of the text information and image information with the given time marker based on a determination that the received health information is at least a threshold value;
    correlating, by the one or more processors using a model, other text information or other image information to the text information or the image information based on the received health information;
    generating, by the one or more processors, a stress indicator based on a determination that the other text information and other image information are correlated to the text information and the image information associated with the received health information;
    displaying, by the one or more processors, the stress indicator on the user device, the stress indicator indicating that the at least one of the text information and image information associated with the given time marker is a health stressor to the user; and
    blocking, by the one or more processors, the at least one of the text information and image information associated with the given time marker from being displayed on the user device.

2. The method of claim 1, comprising one or more of the following steps:
    classifying the text information to produce a first numerical value;
    determining a topic category associated with the text information to produce a second numerical value;
    classifying the image information to produce a third numerical value; and
    forming a first vector comprising the first, second, and third numerical values and the received health information.

3. The method of claim 2, wherein correlating comprises searching a vector space having a plurality of vectors using the received health information of the first vector.

4. The method of claim 2, wherein classifying the text information comprises classifying the text information using a sentiment classifier.

5. The method of claim 4, wherein an output of the sentiment classifier is mapped to numerical values including the first numerical value.

6. The method of claim 4, wherein the sentiment classifier comprises one of a Support Vector Machine (SVM), a Bayesian classifier or Long Short Term Memory (LSTM) derived model.

7. The method of claim 1, wherein the image information comprises video or still image data.

8. The method of claim 1, wherein the image information is viewable through an application on the user device.

9. The method of claim 1, wherein health information comprises one or more of a heart rate, heart rate variability, temperature, stress from EDA activity, user motion, and sleep data.

10. The method of claim 1, wherein the stress indicator comprises a message that notifies the user of the stressor event.

11. An apparatus, comprising:
    a communications interface coupled to a wearable device;
    a display; and
    one or more computing devices coupled to one or more memory devices, the one or more memory devices containing instructions that cause the one or more processing devices to:
    display one or more of text information and image information on the display;
    obtain health information at a given time marker from the wearable device associated with a user during displaying of the one or more of text information and image information;
    associate at least one of the text information and image information with the given time marker based on a determination that the received health information is at least at a threshold value;
    correlate, using a model, other text information or other image information to the text information or the image information based on the received health information;
    generate a stress indicator based on a determination that the other text information and other image information are correlated to the text information and the image information associated with the received health information;

display the stress indicator on the display, the stress indicator indicating that the at least one of the text information and image information associated with the given time marker is a health stressor to the user; and block the at least one of the text information and image information associated with the given time marker from being displayed on the display.

12. The apparatus of claim 11, the one or more instructions cause the one or more processing devices to do one or more of the following operations:

classify the text information to produce a first numerical value;

determine a topic category associated with the text information to produce a second numerical value;

classify the image information to produce a third numerical value; and form a first vector comprising the first, second, and third numerical values and the received health information.

13. The apparatus of claim 12, wherein the instructions cause the one or more processing devices to correlate by searching a vector space having a plurality of vectors using the received health information of the first vector.

14. The apparatus of claim 12, wherein the instructions cause the one or more processing devices to classify the text information by classifying the text information using a sentiment classifier.

15. The apparatus of claim 14, wherein an output of the sentiment classifier is mapped to numerical values including the first numerical value.

16. The apparatus of claim 14, wherein the sentiment classifier comprises one of a Support Vector Machine (SVM), a Bayesian classifier or Long Short Term Memory (LSTM) derived model.

17. The apparatus of claim 11, wherein the image information comprises video or still image data.

18. The apparatus of claim 11, wherein the image information is viewable through an application on the apparatus.

19. The apparatus of claim 11, wherein health information comprises one or more of a heart rate, heart rate variability, temperature, stress from EDA activity, user motion, and sleep data.

20. The apparatus of claim 11, wherein the stress indicator comprises a message that notifies the user of the stressor event.

* * * * *